United States Patent
Bock et al.

(10) Patent No.: US 9,366,809 B1
(45) Date of Patent: Jun. 14, 2016

(54) INTER-GRATING FIBER SPACED MULTI-DRLPG DOPED OPTICAL SENSOR

(71) Applicants: Wojtek J. Bock, Ottawa (CA); Saurabh Mani Tripathi, Kanpur (IN); Predrag Mikulic, Ottawa (CA)

(72) Inventors: Wojtek J. Bock, Ottawa (CA); Saurabh Mani Tripathi, Kanpur (IN); Predrag Mikulic, Ottawa (CA)

(*) Notice: Subject to any disclaimer, the term of this patent is extended or adjusted under 35 U.S.C. 154(b) by 0 days.

(21) Appl. No.: 14/725,256

(22) Filed: May 29, 2015

(51) Int. Cl.
*G02B 6/02* (2006.01)
*G01N 21/41* (2006.01)
*G01N 21/77* (2006.01)

(52) U.S. Cl.
CPC .......... *G02B 6/02176* (2013.01); *G01N 21/412* (2013.01); *G02B 6/0219* (2013.01); *G02B 6/02185* (2013.01); *G01N 2021/7776* (2013.01)

(58) Field of Classification Search
CPC .......... G02B 6/02176; G02B 6/02185; G02B 6/0219; G01N 21/412; G01N 2021/7776
See application file for complete search history.

(56) References Cited

U.S. PATENT DOCUMENTS

| | | | | |
|---|---|---|---|---|
| 7,336,862 B1 * | 2/2008 | Xai | ..................... | G01D 5/35303 385/12 |
| 7,489,835 B1 * | 2/2009 | Xia | ..................... | G01N 21/774 385/12 |
| 2005/0002606 A1 * | 1/2005 | James | ................. | G01D 5/35303 385/31 |

OTHER PUBLICATIONS

Singh et al, "Study and investigation of long period grating as refractive index sensor", In Optik—International Journal for Light and Electron Optics. Apr. 2014 125(7):1860-1863.*
Choudhury et al, "Optimal design of silica-based temperature-insensitive long-period waveguide gratings for realization of athermal refractive-index sensor", In Sensors & Actuators: A. Physical. 2008 141 (2):328-333.*
Jin et al, "Optimal design of temperature-insensitive long period fiber gratings for athermal refractive-index sensor", In Optik—International Journal for Light and Electron Optics. 2011 122(23):2147-2150.*
Singh, "Study of various cladding modes effective refractive indices behavior in long period fiber grating based refractive index sensor: Employing two layer and three layer geometry approach", In Optik—International Journal for Light and Electron Optics. Dec. 2015 126(24):5381-5386.*
Guo et al, "Simultaneous measurement of refractive index and temperature using dualperiod grapefruit microstructured fiber grating", In Optik—International Journal for Light and Electron Optics. Sep. 2013 124(18):3371-3374.*

* cited by examiner

*Primary Examiner* — Ryan Lepisto

(57) ABSTRACT

An optical sensor having dual resonant long period gratings (DRLPGs) separated by an inter-grating fiber spacing IGS of a length and material to provide temperature insensitivity over a wide wavelength range. The materials of the IGS and DRLPGs are such that the difference between the dn/dT of the core and the dn/dT of the cladding in the IGS is opposite in sign to that of the DRLPGs. The DRLPGs and the IGS are also composed of materials and have dimensions such that the turn-around points $\lambda_D$, as well as the general functional form of the respective spectral variation of their propagation constant difference $\Delta\beta$ versus wavelength are substantially similar.

23 Claims, 9 Drawing Sheets

INTER-GRATING FIBER SPACED MULTI-DRLPG DOPED OPTICAL SENSOR

TECHNICAL FIELD

The present invention relates to refractive index measurement, and more particularly, to fiber based optical sensors capable of detecting changes in refractive index while immersed in an analyte.

BACKGROUND

In both the scientific and industrial sectors, conveniently obtaining accurate measurement of refractive index (RI) is of prime importance. In the context of the biological and chemical sciences, optical sensors which measure changes in refractive index are often used to detect elements in a medium by measuring changes in the refractive index of that medium. Consequently, detection of various kinds of elements such as bio-agents and pathogens contained in a medium are detected by RI measuring optical sensors through detection of changes in the medium's effective refractive index caused by the presence of those elements.

Photonic biosensors capable of measuring extremely small changes in the RI of biological/chemical samples have received considerable attention, and a number of optical platforms based on long-period gratings (LPGs), surface-plasmon polariton (SPP), and microstructured fibers have been investigated. Although these sensors are highly sensitive, exhibiting 1000-2000 nm/Refractive Index Units (RIU), often a precise determination of RI needs temperature isolation/calibration, since the RI of the waveguide regions change with temperature.

In the application of known fiber based optical sensors, typically, to measure the RI of a fluid sample, the optical sensor is immersed in the sample, a broadband light source coupled to one end of the sensor then transmits light through the sensor which is detected by a detector coupled to the other end of the sensor. The optical properties, i.e. the spectral transmittance, of the combination of the optical sensor and the sample will change based on the effective refractive index of the sample in the ambient region just outside the cladding of the fiber. Presence of an analyte in the sample being measured changes the RI of the sample, which affects the interaction of the sample with the evanescent field of the cladding mode which extends into the sample. Such changes in interaction change the "effective" index" of refraction through which the cladding mode propagates, which in turn shifts the resonance wavelength(s) and the resonance minima observed. Specific resonance minima of the spectral transmittance whose value of wavelength vary as a function of RI are typically used to determine the RI of samples and some optical sensor systems specifically rely upon the values of a plurality of these minima to provide a more accurate RI measurement.

The spectrum of the light transmitted through the optical sensor is not solely dependent on the effective refractive index of the sample but also on the temperature of the optical sensor. In particular the various resonance minima used to determine the RI of the sample can shift as a consequence of changing temperature. In order to ensure that the refractive index is measured as accurately as possible it is desirable to compensate for any change in the transmitted spectrum due to temperature. Obtaining accurate measurements independent of temperature can be approached utilizing one or more of a few broad techniques which include temperature isolation and regulation, optical sensor spectral transmittance temperature insensitivity, and mathematical compensation and calibration. Insofar as an optical sensor can be physically made to be temperature insensitive, the need for temperature isolation and regulation and/or mathematical compensation and calibrations is reduced as are measurement costs and time.

A number of different specific ways to facilitate temperature compensation have been suggested, such as combining fiber Bragg gratings (FBG) with LPGs in optical waveguides, cascaded LPGs in double cladding fiber, $\pi/2$ phase shifted dual resonance LPG (DRLPG), among others. All of these schemes, however, rely on measuring two parameters and calculating the desired measurement using a 2×2 matrix. This increases the complexity of the detection system. Other methods applicable to LPGs involve suitably chosen cladding and core materials with opposite thermo-optic coefficients and an overall coating of the sensor with a suitable composite material to compensate for the temperature-induced wavelength shifts. The requirement of custom-made fibers in the former increases the cost and fabrication time of the sensor while the extra coating in the latter reduces the RI sensitivity. Furthermore, often an attempt to increase RI sensitivity results in increased temperature sensitivity. It also is possible to fabricate and configure an optical sensor in such a way that it exhibits temperature insensitivity at a particular wavelength however this is not effective with approaches relying on multiple resonance minima.

It would be desirable to have an alternative to the above mentioned schemes, in particular one which would not require a 2×2 matrix, which is cost effective, and exhibits spectral temperature insensitivity over a wavelength range rather than at a single wavelength to enable use of multiple resonance minima and hence obtain measurements which simultaneously exhibit high RI sensitivity and high temperature insensitivity.

SUMMARY

To simultaneously address the issues of precision and temperature insensitivity, an optical sensor according to the invention broadly includes at least two concatenated DRLPGs optically coupled to one another by a length of inter-grating fiber composed of a fiber having an opposite temperature dependence from that of the DRLPGs.

According to a first broad aspect of the invention there is provided a fiber based optical sensor for measuring refractive index (RI), the optical sensor comprising: a plurality of dual resonant long period grating fiber portions (DRLPG), each having DRLPG core and DRLPG cladding; and an inter-grating fiber spacing (IGS) optically coupled between the plurality of DRLPGs, having an IGS core and an IGS cladding such that a difference between an overall thermo-optic coefficient (dn/dT) of the IGS core and a dn/dT of the IGS cladding, is of a sign opposite to a difference between a dn/dT of the DRLPG core and a dn/dT of the DRLPG cladding, the length of the IGS being such that the optical sensor exhibits a substantial temperature insensitivity over a wide wavelength range.

In some embodiments the IGS comprises $B_2O_3$ doped germaniosilicate core fiber.

In some embodiments each DRLPG is fabricated from germaniosilicate core fiber.

In some embodiments the IGS cladding and the DRLPG cladding each comprise $SiO_2$, and the DRLPG core comprises $GeO_2$, such that the difference between the (dn/dT) of the IGS core and the dn/dT of the IGS cladding is negative, and the difference between the dn/dT of the DRLPG core and the dn/dT of the DRLPG cladding is positive.

In some embodiments the IGS core comprises $GeO_2$, each DRLPG core comprises $B_2O_3$, and the IGS cladding and the DRLPG cladding each comprise $SiO_2$, such that the difference between the (dn/dT) of the IGS core and the dn/dT of the IGS cladding is positive, and the difference between the dn/dT of the DRLPG core and the dn/dT of the DRLPG cladding is negative.

In some embodiments the turn-around points of the propagation constant difference curves of the IGS and the plurality of DRLPGs coincide, while in some embodiments turn-around points of the propagation constant difference curves of the IGS and the plurality of DRLPGs are substantially equal.

In some embodiments the wide wavelength range is 200 nm and in some embodiments the wide wavelength range is substantially 100 nm on either side of the turn-around points of the propagation constant difference curves of the IGS and the plurality of DRLPGs.

In some embodiments a temperature dependence of the propagation constant difference curve of the IGS doped with $B_2O_3$ is larger than a temperature dependence of the propagation constant difference curve of the plurality of DRLPGs.

In some embodiments the plurality of DRLPGs comprise two DRLPGs.

In some embodiments a ratio of a slope of a propagation constant difference curve of the IGS to a slope of a propagation constant difference curve of the plurality of DRLPGs is substantially constant over the wide wavelength range.

In some embodiments the IGS comprises single mode PS-1250/1500™ fiber, each DRLPG comprises standard SMF-28™ fiber, a period of the gratings of the DRLPGs is 226.8 µm, each DRLPG is 4 cm in length, and the IGS is 8.9 cm in length.

In some embodiments the core radius of the IGS is substantially equal to 4.95 µm, the cladding radius of the IGS is substantially equal to 62.5 µm, the core radius of the DRLPGs is substantially equal to 4.1 µm, the unetched cladding radius of the DRLPGs is substantially equal to 62.5 µm, and the etched cladding radius of the DRLPGs is substantially equal to 55 µm.

BRIEF DESCRIPTION OF THE DRAWINGS

The features and advantages will become more apparent from the following detailed description of the preferred embodiment(s) with reference to the attached figures, wherein.

DETAILED DESCRIPTION OF THE PREFERRED EMBODIMENTS

Figure 1A:
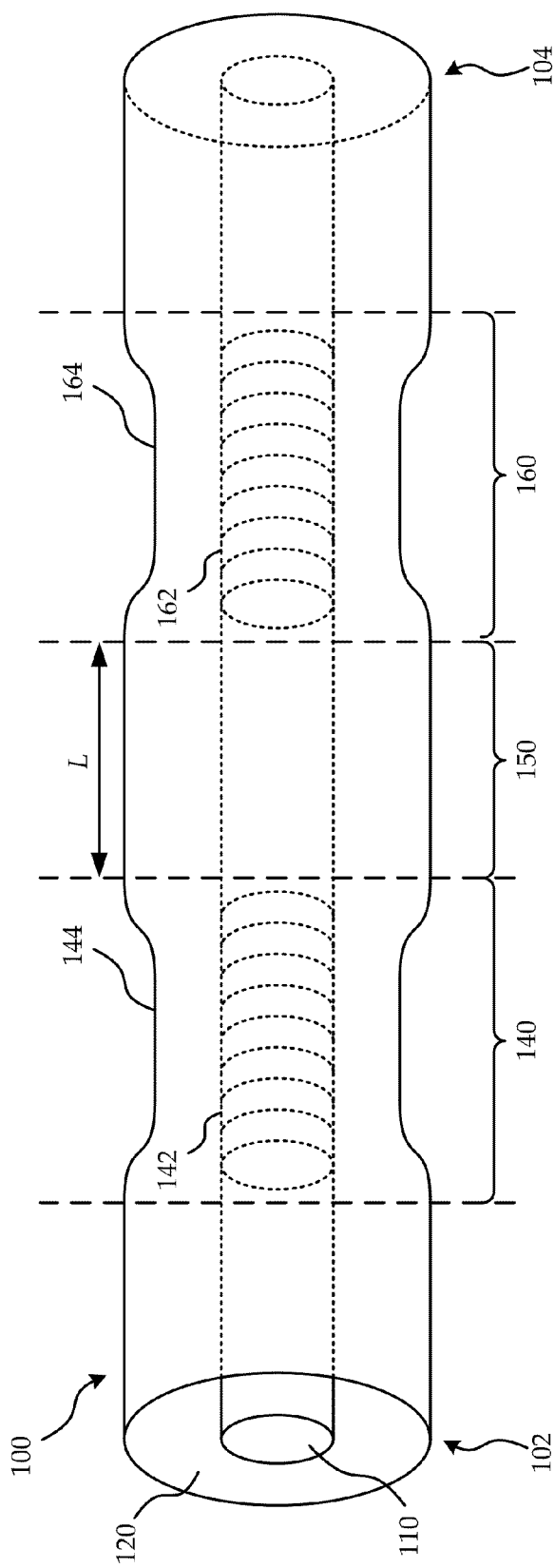
FIG. 1A is a perspective view of a multi-DRLPG optical sensor.

A convenient, accurate, and cost-effective wide wavelength range temperature insensitive RI sensor would be preferable to the above mentioned sensor schemes. As described herein below provided is a simple, cost effective, temperature-insensitive, ultrasensitive RI sensor, using concatenated DRLPGs spaced apart by an inter-grating fiber spacing of opposite temperature sensitivity to that of the DRLPGs.

In order to illustrate fully the embodiment of the invention depicted in FIG. 5, an optical sensor generally indicated by numeral 100, will now be described in terms of its structure with reference to FIG. 1A.

The optical sensor 100 is comprised of optical fiber having a core 110 and a cladding 120 and having a first end 102, a second end 104 and which includes a first dual-resonant long period grating (DRLPG) 140, an inter-grating fiber spacing (IGS) 150 of length L (alternatively referred with the symbol "l"), and a second DRLPG 160. The first DRLPG 140 is optically coupled to the IGS 150 and the IGS 150 is optically coupled to the second DRLPG 160. The IGS 150 is made of a fiber of substantially the same composition as that of the first and second DRLPGs 140, 160.

The first DRLPG 140 includes an LPG 142 formed in the core 110 and a recessed portion 144 formed in the cladding 120, where the thickness of the cladding is reduced in the region of the DRLPG 140. As shown in FIG. 1B, the cladding 120 of the optical sensor 100 has a thickness $t_r$ in the recessed portions 144, 164 which is less than the thickness $t_o$ of portions located elsewhere along the optical sensor 100.

Similarly the second DRLPG 160 includes an LPG 162 formed in the core 110 and in the region of the second DRLPG 160 a recessed portion 164 formed in the cladding 120.

Figure 1B:
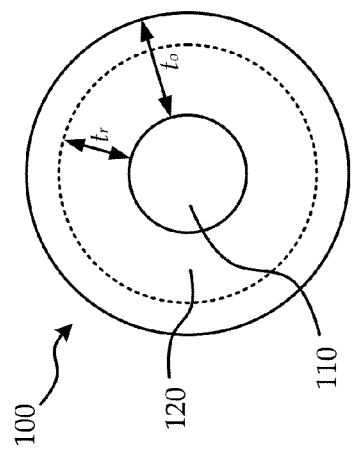
FIG. 1B is a longitudinal view of the multi-DRLPG optical sensor depicted in FIG. 1A.

With reference to FIGS. 1A and 1B the optical sensor 100 will now be described in terms of its function.

By way of explanation of the function of a multi-DRLPG as for example illustrated in FIGS. 1A and 1B, the function of LPGs and single DRLPGs will now briefly be discussed. The general principles of individual LPGs and DRLPGs are known to skilled persons in the art.

An LPG sensor senses characteristics of the surrounding medium by coupling part of the optical field from the fiber core mode to the cladding mode, whose purpose is to interact with the surrounding medium. The geometry of the LPG determines the wavelength or wavelengths $\lambda_R$ at which this coupling occurs, refer to Eq. [1]. In particular the effective indices of refraction of the core and cladding.

$$\lambda_R = \Lambda \left( n_{eff}^{co} - n_{eff}^{cl} + \frac{k_{co-co} - k_{cl-cl}}{k_0} \right) \quad [1]$$

Where $n_{eff}^{co}$ and $n_{eff}^{cl}$ are respectively the effective refractive indices of the core and the cladding mode; $\Lambda$ is the grating period; and $k_{co-co}$ and $k_{cl-cl}$ are the self-coupling coefficients of the core mode and the cladding mode, respectively; and $k_0$ is the free-space wavenumber. Once coupled into the cladding mode a small portion of the incident optical field travels outside of the optical fiber and interacts with the surrounding medium. The index of refraction of the surrounding medium changes the effective refractive index (RI) of the cladding mode, $n_{eff}^{cl}$, and subsequently, the resonant wavelength(s) of the sensor. Changes in ambient RI are thus measured by detecting changes in the resonant wavelength(s). A drawback of the LPG sensor which couples part of the optical field into the cladding mode is that by doing so it introduces multiple optical paths allowing for a temperature dependent phase shift between the core mode and the excited cladding mode(s) which alters the transmission spectrum of the sensor.

A DRLPG 140 such as that of FIG. 1A and FIG. 1B is formed from an LPG with a reduced thickness $t_r$ of the cladding 120 in the region of the LPG which results in two resonance wavelengths $\lambda_{R1}$ and $\lambda_{R2}$ at which the optical field is coupled to the same higher order cladding mode. More particularly, the etching process results in tuning the single resonance into two resonance wavelengths $\lambda_{R1}$ and $\lambda_{R2}$ in the low loss window of telecommunication wavelengths for water as a surrounding medium.

Figure 2:
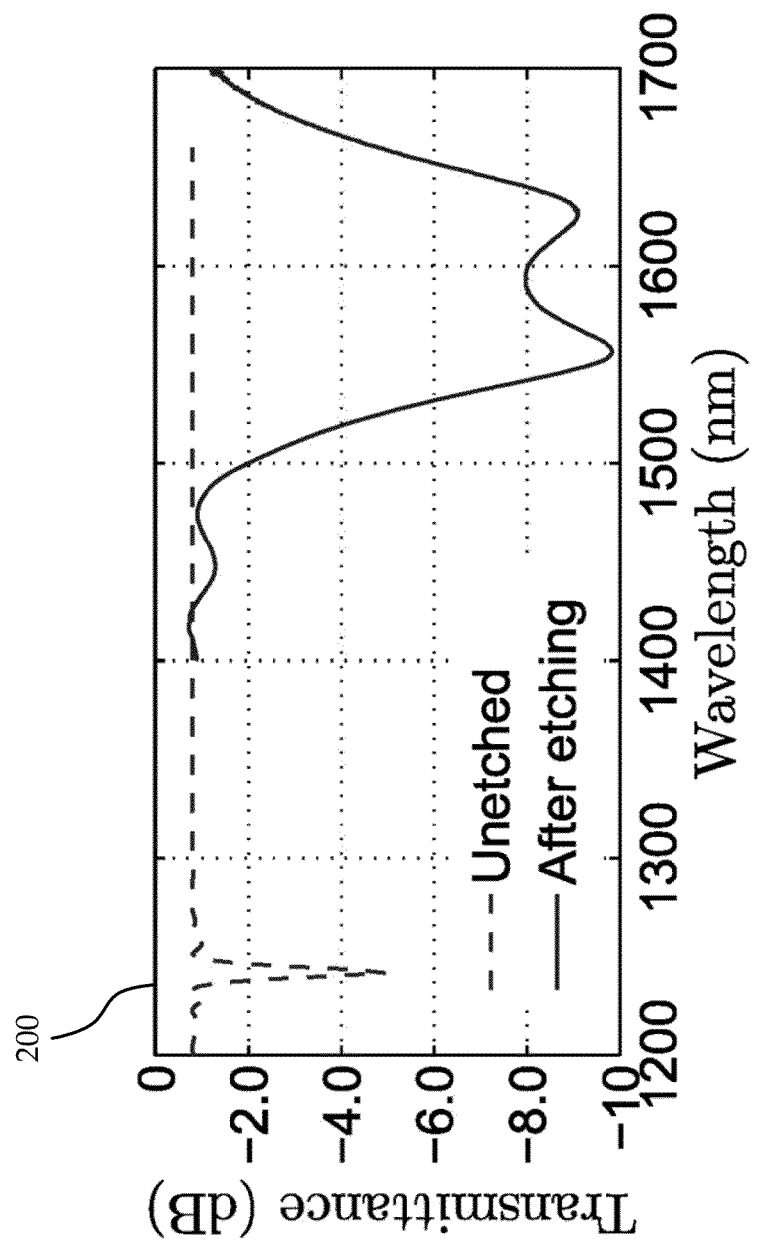
FIG. 2 is a graph illustrating the transmission spectra of an LPG and an etched LPG (DRLPG)

As shown in the graph 200 of FIG. 2, the unetched LPG has a single resonant minimum while the etched LPG (DRLPG) exhibits dual resonance, i.e. two resonance minima. Multiple resonance minima allow for more precise RI measurement by providing multiple points to observe for shifts in response to changes in RI of the sample, and double the sensitivity by measuring one shift in relation to another. It should be noted that for an unetched LPG every cladding mode will have one and only one resonance wavelength whereas for a dual resonance LPG (DRLPG) a single cladding mode has resonances at two different wavelengths and these two resonances shift in opposite directions as the RI of the analyte changes. This opposite movement of the two resonance wavelengths doubles the sensitivity making DRLPG based optical sensors preferable.

With reference once again to FIG. 1A and FIG. 1B, when in use the first end 102 of the optical sensor 100 is coupled to a broadband light source (not shown) and the second end 104 of the optical sensor 100 is coupled to a spectrum analyzer. As described in association with single LPGs and single DRLPGs above, the purpose of the first DRLPG 140 is to couple a portion of the core mode into a higher order cladding mode(s) by redirecting part of an optical field from the core 110 to the cladding 120 where a portion thereof interacts with the ambient region in the sample just outside the cladding 120. The second DRLPG 160 serves to couple the higher order cladding mode(s) back to the core mode thereby redirecting the optical field from the cladding 120 to the core 110. The IGS 150 keeps the modes in their respective core or cladding regions of the optical sensor fiber and provides an extra phase difference between the core and cladding modes as a function of its length and material properties. By adjusting the length of the IGS 150, temperature-induced phase changes in the grating regions 140, 160 can be compensated with phase changes introduced by the IGS 150 and in particular, the optical sensor 100 can be made completely temperature insensitive at a specific wavelength and substantially temperature independent over or below a specific wavelength, without affecting the RI sensitivity of the structure.

Figure 3:
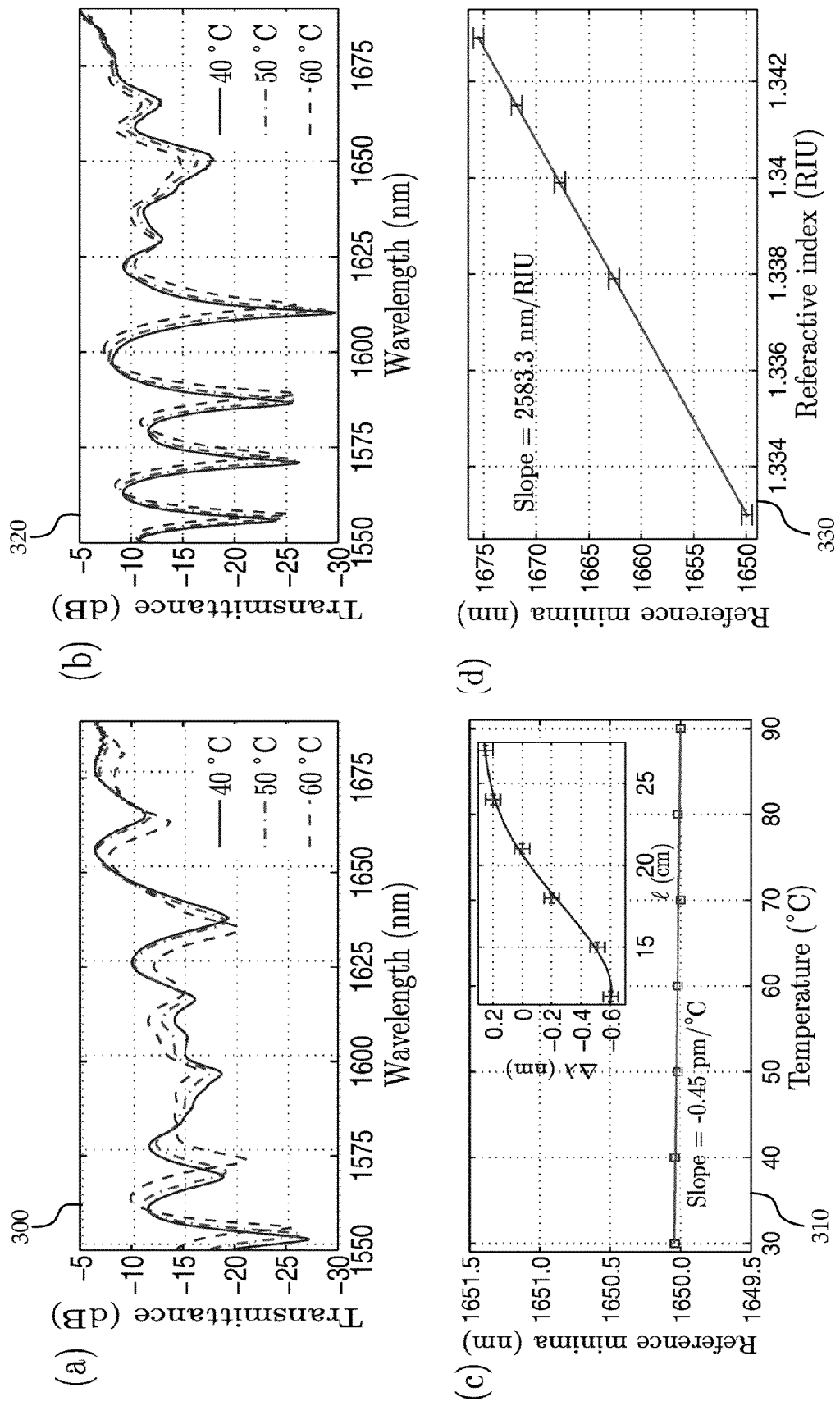
FIG. 3 shows (a) a graph illustrating the experimental transmission spectrum of an optical sensor as shown in FIGS. 1A and 1B with an inter-grating fiber spacing of 18 cm; (b) a graph illustrating the experimental transmission spectrum of an optical sensor as shown in FIGS. 1A and 1B with an inter-grating fiber spacing of 21 cm, chosen to counteract the temperature-inducted spectral shift of a DRLPG; (c) a graph illustrating measurements of the variation of reference minima near 1650 nm versus temperature for an optical sensor as shown in FIGS. 1A and 1B with the inter-grating fiber spacing of 21 cm; and (d) a graph illustrating measurements of the variation of reference minima near 1650 nm versus ambient refractive index for an optical sensor as shown in FIGS. 1A and 1B with the inter-grating fiber spacing of 21 cm.

With reference to FIG. 3, an experiment which was conducted in which sensors according to FIG. 1A and FIG. 1B were constructed by selecting a pair of DRLPGs 140 160 with substantially identical transmission spectrum and splicing the pair of DRLPGs 140 160 axially with varying IGS 150 in between them, will now be discussed. The sensors were passed through a heating tube filled with water to measure their temperature response.

Bends across the sensing region were avoided by maintaining a constant tension throughout the experiments by fixing the fiber near one end of the DRLPG to a stationary stage and applying a fixed force near the other end of it. Light was launched into the fiber using an Agilent™-83437A broadband source and the transmission spectrum was recorded using an Agilent™-86142B optical spectrum analyzer and Agilent™-N1031A BenchLink Lightwave™ application software having a spectral resolution of 10 pm.

FIG. 3 shows a graph 300 of the transmission spectrum for three different temperatures (T=40° C., 50° C., and 60° C.) recorded for an IGS 150 having a length of 18 cm (FIG. 3(a)) and a similar graph 320 for an IGS 150 having a length of 21 cm (FIG. 3(b)), each with a wavelength resolution of 0.05 nm. Compared to the sensitivity of a single DRLPG (1.03 nm/° C.), FIG. 3(a) shows a reduced temperature sensitivity of 0.17 nm/° C. at $\lambda$=1627 nm for an IGS 150 of 18 cm.

Increasing the length of the IGS 150 further to 21 cm, it can be observed in graph 320 of FIG. 3(b) that there are nearly temperature insensitive minima (maxima) 522 above 1627 nm (initial resonance minima of single DRLPG), most prominently for transmission minima at 1650 nm.

FIG. 3(c) shows a graph 310 of the variation of reference minima near 1650 nm for l=21 cm as a function of temperature using a wavelength resolution of 0.02 nm, which shows a temperature sensitivity of −0.45 pm/° C., a reduction by a factor of $4 \times 10^4$ compared to 1.03 nm/° C. obtained for a single DRLPG.

Increasing the length of the IGS 150 even further resulted in a red shift with increasing temperature. This behavior is plotted in the inset of the graph 310 of FIG. 3(b) which shows the measured resonance wavelength shift ($\Delta\lambda$) corresponding to the maxima/minima near 1650 nm for different lengths l of IGS 150, for a temperature increase of 20° C., which shows that a complete temperature insensitivity is possible near l~20.7 cm.

In FIG. 3(*d*) a graph 330 shows the 1650 nm reference minima for various ambient RI within the biologically relevant RI range of 1.333-1.343. As can be seen from the graph 330, the slope is 2583.3 nm/RIU. The increase in the RI sensitivity for sensors incorporating the IGS 150 can be attributed to the fact that for the current measurements, the resonance (reference) wavelength (1650 nm) is slightly higher than that of the single DRLPG (1627 nm), leading to an increased cladding mode evanescent field in the ambient region. The RI sensitivity can be further improved by (i) reducing the grating period to couple the power to even higher order cladding modes and (ii) operating the gratings near $\lambda_D$ to enhance the spectral shift.

To understand the origin of temperature insensitivity of the sensor 100 mathematically, an optical fiber with core 110 and cladding 120 regions made of 4.1 mol. % $GeO_2$ doped $SiO_2$ and fused $SiO_2$, respectively, their radii ($r_c$ and $r_{cl}$) as 4.1 and 62.5 μm, respectively, and ambient RI as 1.333 was considered. The overall transmission of the sensor mainly depends upon two factors: (i) the phase matching within the grating regions 140, 160 (which are used to excite and recouple cladding mode back to the core mode) and (ii) modal interference within the IGS 150 region. Both of these factors are governed by the propagation constant difference between the core and cladding modes $\Delta\beta = \beta_c - \beta_{cl}$. The transmitted field amplitudes of core and cladding modes ($A_c$ and $A_{cl}$) are obtained using $$\begin{bmatrix} A_c \\ A_{cl} \end{bmatrix} = T_{LPG} \times \begin{bmatrix} e^{i\beta_c l} & 0 \\ 0 & e^{i\beta_{cl} l} \end{bmatrix} \times T_{LPG} \times \begin{bmatrix} 1 \\ 0 \end{bmatrix}, \quad [2]$$

where $T_{LPG}$ is the transfer matrix of LPG given by $$T_{LPG} = \begin{bmatrix} \cos\gamma L_g + i\frac{\delta}{\gamma}\sin\gamma L_g & i\frac{\kappa}{\gamma}\sin\gamma L_g \\ i\frac{\kappa}{\gamma}\sin\gamma L_g & \cos\gamma L_g - i\frac{\delta}{\gamma}\sin\gamma L_g \end{bmatrix} \quad [3]$$

with κ being the cross coupling coefficient between the core and the cladding mode given by, $$\kappa = \frac{\omega\varepsilon_0 n_\omega^2}{2} \int_0^{2\pi} \int_0^\infty \sigma \psi_{co} \psi'_{cl} r \, dr \, d\theta \quad [4]$$

$\varepsilon_0 (= 8.85 \times 10^{-12}$ F/m) is the permittivity of free space, $n_{co}$ and σ are the core refractive index and grating strength, respectively, δ is the detuning parameter given by $$\delta = \frac{1}{2}\left(\beta_{co} + \kappa_{co-co} - \beta_{cl} - \kappa_{cl-cl} - \frac{2\pi}{\Lambda}\right)$$

with $\gamma = \sqrt{\kappa^2 + \delta^2}$, and Λ, $\beta_{co}$, $\beta_{cl}$, $\kappa_{co-co}$, and $\kappa_{cl-cl}$ being the grating period, propagation constant of core mode, cladding mode, self-modal coupling coefficient of the core mode and cladding mode, respectively.

Figure 4:
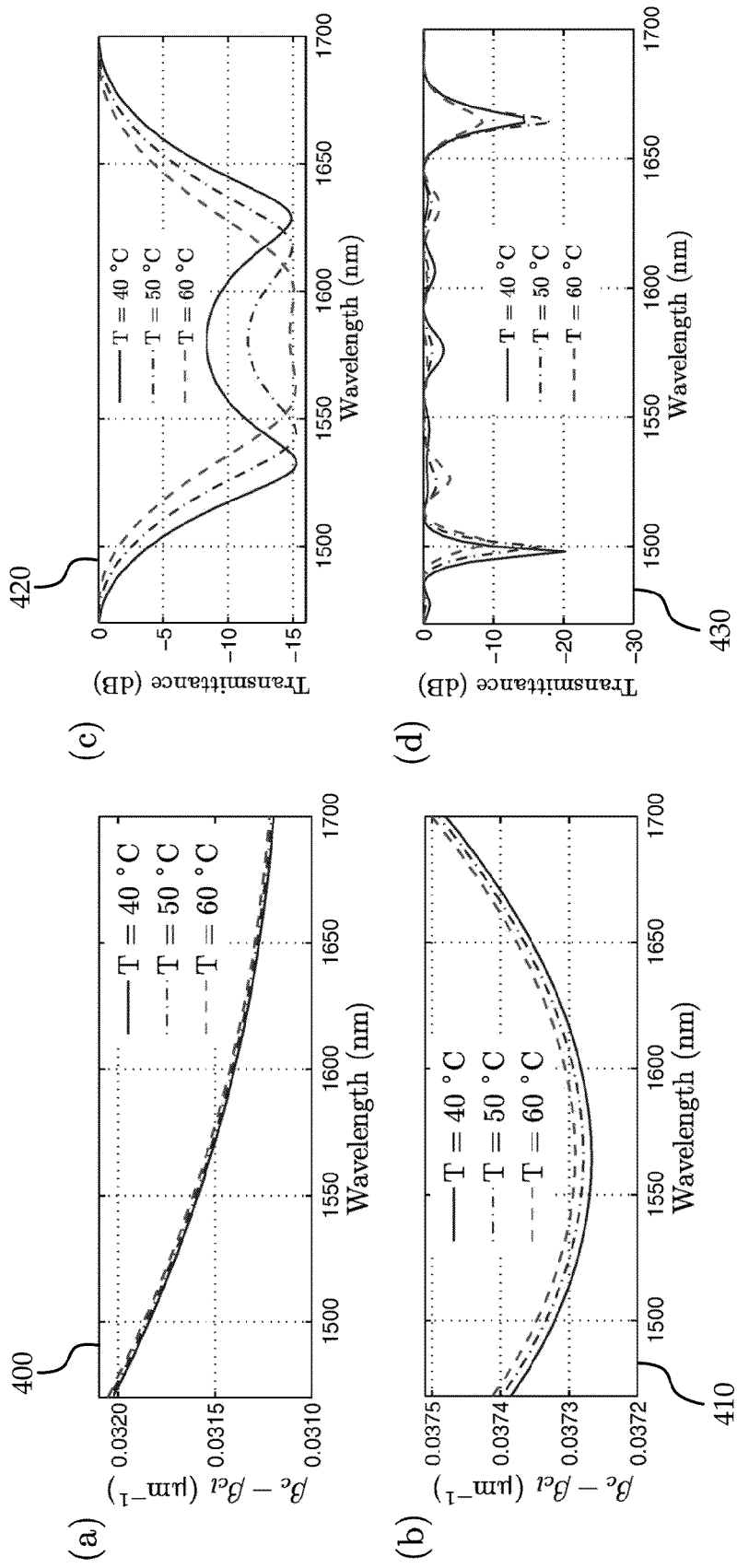
FIG. 4 shows (a) a graph illustrating an example calculation of the spectral variation of the propagation constant difference between the core mode and the cladding mode in an unetched fiber; (b) a graph illustrating an example calculation of the spectral variation of the propagation constant difference between the core mode and the cladding mode in an etched fiber; (c) a graph illustrating an example calculated transmission spectrum expected for a single LPG in etched fiber; and (d) a graph illustrating an example calculated transmission spectrum expected for concatenated LPGs in etched fiber separated by an unetched fiber of a certain length.

FIG. 4(*a*) shows a graph 400 of the spectral variation of Δβ, considering $LP_{010}$ cladding mode in an unetched region (such as IGS 150) of sensor 100 with an unetched cladding 120 of radius $r_{cl}$=62.5 μm. FIG. 4(*b*) shows a graph 410 of the spectral variation of Δβ, considering $LP_{010}$ cladding mode for sensor 100 in the regions 140, 160 with etched recessed portions 144, 164 in the cladding having an etched radius $r_{cl}$=55 μm.

The graph 410 of FIG. 4(*b*) shows a turnaround wavelength $\lambda_D$ near 1570 nm, with a negative slope of the Δβ versus λ curve for $\lambda < \lambda_D$ and a positive slope for $\lambda > \lambda_D$. The opposite slopes of Δβ versus λ curve give rise to opposite spectral shifts for the resonance minimum of the DRLPG written in a fiber with appropriate cladding thickness, supporting the dual resonance. The graph 400 of FIG. 4(*a*) on the other hand shows a monotonic function of negative slope over the entire wavelength range. For $\lambda > \lambda_D$ the spectral shifts introduced by an unetched IGS region 150, therefore, counteract the spectral shifts induced by the DRLPGs. At an appropriate length l of IGS 150, the two spectral shifts substantially nullify each other, producing temperature insensitive maxima/minima.

To show this behavior mathematically, graph 420 of FIG. 4(*c*) depicts the transmission spectrum of a single LPG with etched cladding i.e. a single DRLPG. The grating strength, period, and length have been taken as $4.4 \times 10^{-5}$, 166.8 μm, and 4 cm, respectively. Finally, the graph in FIG. 4(*d*) depicts the transmission spectrum of concatenated DRLPGs 140, 160 in etched fibers having etched radii $r_{cl}$=55 μm separated by an IGS 150 of 5.2 cm in unetched fiber. Substantially temperature insensitive minima (for $\lambda > \lambda_D$) induced by the IGS 150 are obtained at 1663 nm. Using known LPG parameters, therefore, an appropriate l can be calculated using Eq. [2]. For unknown LPG parameters, on the other hand, l can be interpolated from the values of lengths of IGSs 150 of sensors showing opposite sensitivities for $\lambda > \lambda_D$.

A method of manufacturing an optical sensor 100 will now be described with reference to FIG. 1A, FIG. 1B, and FIG. 2.

Photo-sensitive DRLPGs 140, 160 can be fabricated in hydrogen loaded SMF-28™ (Corning, N.Y., 14831, USA), using a chromium amplitude mask (Λ=226.8 μm) and KrF excimer laser (Lumonics Lasers: Pulse Master-840™) emitting at 248 nm at a pulse repetition rate of 100 Hz, pulse duration of 12 ns, and peak pulse energy of 10 mJ. The grating length can be approximately 5 cm. The LPGs are then annealed at 150° C. for ~4 h to release excess hydrogen, stabilizing their optical properties. The LPGs so fabricated had a single resonance wavelength ($\lambda_R$) near 1245 nm as is clearly shown in the graph 200 of FIG. 2. To obtain a dual resonance behavior, the cladding 120 of the fiber was slowly etched in 4% HF acid for ~3 h. This shifted the AR close to its turning point ($\lambda_D$) of ~1.595 μm. FIG. 2 shows a graph 200 including a plot of the transmittance of the fiber after the etching process. The typical RI and temperature sensitivities, recorded for the lower $\lambda_R$ (=1557 nm), are 1837 nm/RIU and 0.95 nm/° C. and for the upper $\lambda_R$ (=1627 nm) are 2464 nm/RIU and 1.03 nm/° C., respectively.

The optical sensor of FIG. 1A and FIG. 1B shows relative temperature insensitivity for $\lambda > \lambda_D$ and substantial temperature insensitivity for a particular wavelength which can be effected by use of an appropriate length l of the IGS 150.

An optical sensor according to an embodiment of the invention and generally indicated by numeral 500 based on two concatenated DRLPGs with an inter-grating fiber spacing of suitably chosen material and length, will now be discussed with reference to FIG. 5. Optical sensors based on the embodiment depicted in FIG. 5, can advantageously be relatively simple to fabricate, cost effective, substantially temperature-insensitive over a wide-wavelength range (1500-1700 nm), and yet remain ultrasensitive to RI.

The optical sensor 500 is comprised of optical fiber having a core 510 and a cladding 520 and having a first end 502, a second end 504, and which includes a first dual-resonant long period grating (DRLPG) 540, a doped inter-grating fiber spacing (IGS) 550, and a second DRLPG 560. The first DRLPG 540 is optically coupled to the IGS 550 and the IGS 550 is optically coupled to the second DRLPG 560.

The IGS 550 is made of a fiber of sufficiently different composition from that of the first and second DRLPGs 540, 560 such that they have opposite temperature sensitivity in accordance with the discussion below regarding function. In some embodiments the optical fiber of the optical sensor 500 including the DRLPGs 540, 560 are composed of standard single mode fiber such as SMF-28™ with germaniosilicate core (doped with $GeO_2$) whereas the IGS 550 is composed of Boron doped ($B_2O_3$) germaniosilicate fiber such as PS-1250/1500™.

The first DRLPG 540 includes an LPG 542 formed in the core 510 and a recessed portion 544 formed in the cladding 520, where the thickness of the cladding is reduced in the region of the DRLPG 540 similar to the etching described in association with FIG. 1A and FIG. 1B.

Similarly the second DRLPG 560 includes an LPG 562 formed in the core 510 and in the region of the second DRLPG 560 a recessed portion 564 formed in the cladding 520.

The optical sensor 500 will now be described in terms of function. When the optical sensor 500 is in use, the first end 502 of the optical sensor 500 is coupled to a broadband light source (not shown) and the second end 504 of the optical sensor 500 is coupled to a spectrum analyzer. As described in association with single DRLPGs above, the purpose of the first DRLPG 540 is to couple a portion of the core mode into a higher order cladding mode by redirecting part of an optical field from a core mode to a cladding mode a portion thereof which interacts with the ambient region in the sample just outside the cladding 520. The second DRLPG 560 serves to couple the higher order cladding mode back to the core mode thereby redirecting the optical field from the cladding 520 to the core 510. The IGS 550 keeps the modes in their respective core or cladding regions of the optical sensor fiber and provides an extra phase difference between the core and cladding modes as a function of its length and particular material properties. By adjusting the length of the IGS 550, temperature-induced phase changes in the grating regions can be compensated with phase changes introduced by the IGS 550 and in particular, the optical sensor 500 can be made substantially temperature insensitive over a wavelength range as described further below, without affecting the RI sensitivity of the structure.

By using a $B_2O_3$ doped germaniosilicate core single-mode fiber as the inter-grating material of the IGS 550, instead of a fiber with the same core material as the DRLPG 540, 560, a large and opposite temperature dependent spectral shift introduced by the inter-grating material counteracts the temperature dependent spectral shifts induced in the DRLPG 540, 560 regions, effectively nullifying the overall temperature dependent spectral shift of the optical sensor 500 over a large wavelength range.

The fiber used for the IGS 550 is made of a material that exhibits an opposite temperature sensitivity to that of the DRLPG structures 540, 560. In the example embodiment depicted in FIG. 5, the material used for the IGS 550 is a $B_2O_3$ doped germaniosilicate core single-mode fiber. Due to the negative thermo-optic coefficient (dn/dT) of $B_2O_3$ ($-350 \times 10^{-7}/°$ C.) and positive dn/dT of $GeO_2$ ($+194 \times 10^{-7}/°$ C.) the overall thermo-optic coefficient of the core region 510 of $B_2O_3$ doped germaniosilicate single mode fiber (PS-1250/1500™) is less than that of the fiber's $SiO_2$ cladding region 520 (dn/dT=$+102 \times 10^{-7}/°$ C.). The lower dn/dT of the core region, relative to the fiber's cladding region, gives rise to the negative temperature sensitivity of the LPGs fabricated in $B_2O_3$ doped germaniosilicate fibers. The dn/dT of a germaniosilicate core 510 of standard SMFs (e.g. SMF-28™), on the other hand, is greater than the dn/dT in its cladding region 520 due to the large positive dn/dT of the $GeO_2$, resulting in the positive temperature sensitivity of the LPGs fabricated in germaniosilicate fibers.

Figure 5:
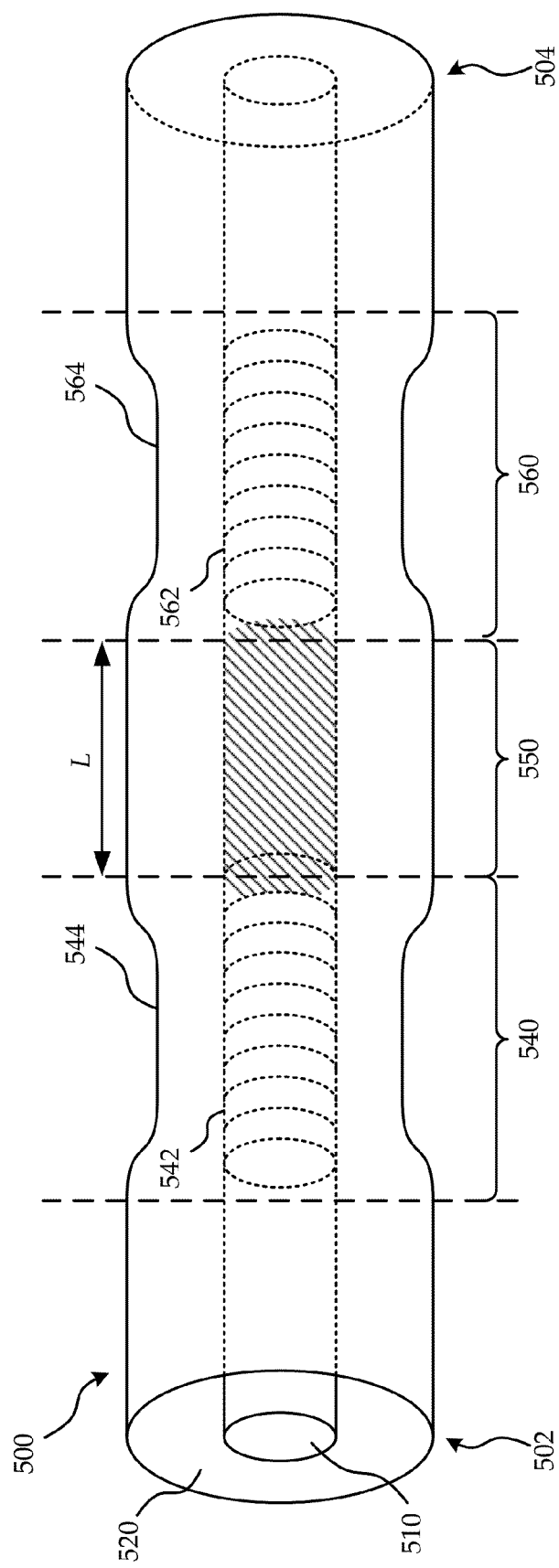
FIG. 5 is a perspective view of an inter-grating fiber spaced multi-DRLPG doped optical sensor according to an embodiment of the invention.

This general temperature dependence exhibited by known LPGs is exploited in the configuration of FIG. 5 which combines between two DRLPGs 540, 560 of one temperature dependence a doped IGS 550 of opposite temperature dependence. As further discussed below certain adjustments are made to ensure substantial temperature insensitivity over a wide wavelength range.

FIG. 6(a) depicts a graph 600 of the spectral variation of the propagation constant difference $\Delta \beta$ of a germaniosilicate fiber (fiber-G) with its core composed of 4.1 mole % $GeO_2$ doped $SiO_2$, cladding made of fused $SiO_2$, core and cladding diameters 8.2 μm and 125 μm, respectively, for a number of temperatures. FIG. 6(b) depicts a graph 610 of the spectral variation of the propagation constant difference $\Delta \beta$ of a $B_2O_3$ doped germaniosilicate fiber (fiber-B) with the core composition of 9.7 mole % $B_2O_3$ in 4.03 mole % $GeO_2$ and 86.27 mole % $SiO_2$, for a number of temperatures.

Considering first, two LPGs fabricated in fiber-G separated by length l of fiber-B, the transmitted optical power of such a sensor depends mainly upon two factors (i) phase matching within the grating regions (used for cladding mode excitation and recoupling to the core mode) and (ii) modal interference within the IGS region. Both of these factors are, in turn, governed by the propagation constant difference $\Delta \beta$ ($\Delta \beta = \beta_{co} - \beta_{cl}$) between the core and cladding modes involved.

As can be seen from the graphs 600, 610 in FIG. 6(a) and FIG. 6(b), both these fibers show a turn-around behavior where $\Delta \beta$ is minimum at wavelength $\lambda_D$~1575 nm, however for fiber-G, $\Delta \beta$ increases with increasing temperature whereas for fiber-B it decreases with increasing temperature. For complete temperature insensitivity on either side of $\lambda_D$, the $\lambda_D$ of the two curves must coincide. If the $\lambda_D$ of the two curves do not coincide, temperature insensitivity will only result outside of the range between and including the $\lambda_D$ of the two curves, leading to substantial temperature insensitivity over two wide wavelength ranges.

By taking an appropriate core and cladding radii of the two fibers, taking into account their particular material composition, the $\lambda_D$ of the two curves can be made to coincide. In this case, with the doping and compositions as outlined above, the core and cladding radii of fiber-G are chosen to be 4.1 μm and 55 μm and for fiber-B chosen as 4.95 μm and 62.5 μm, respectively, to obtain coincidental $\lambda_D$.

Figure 6:
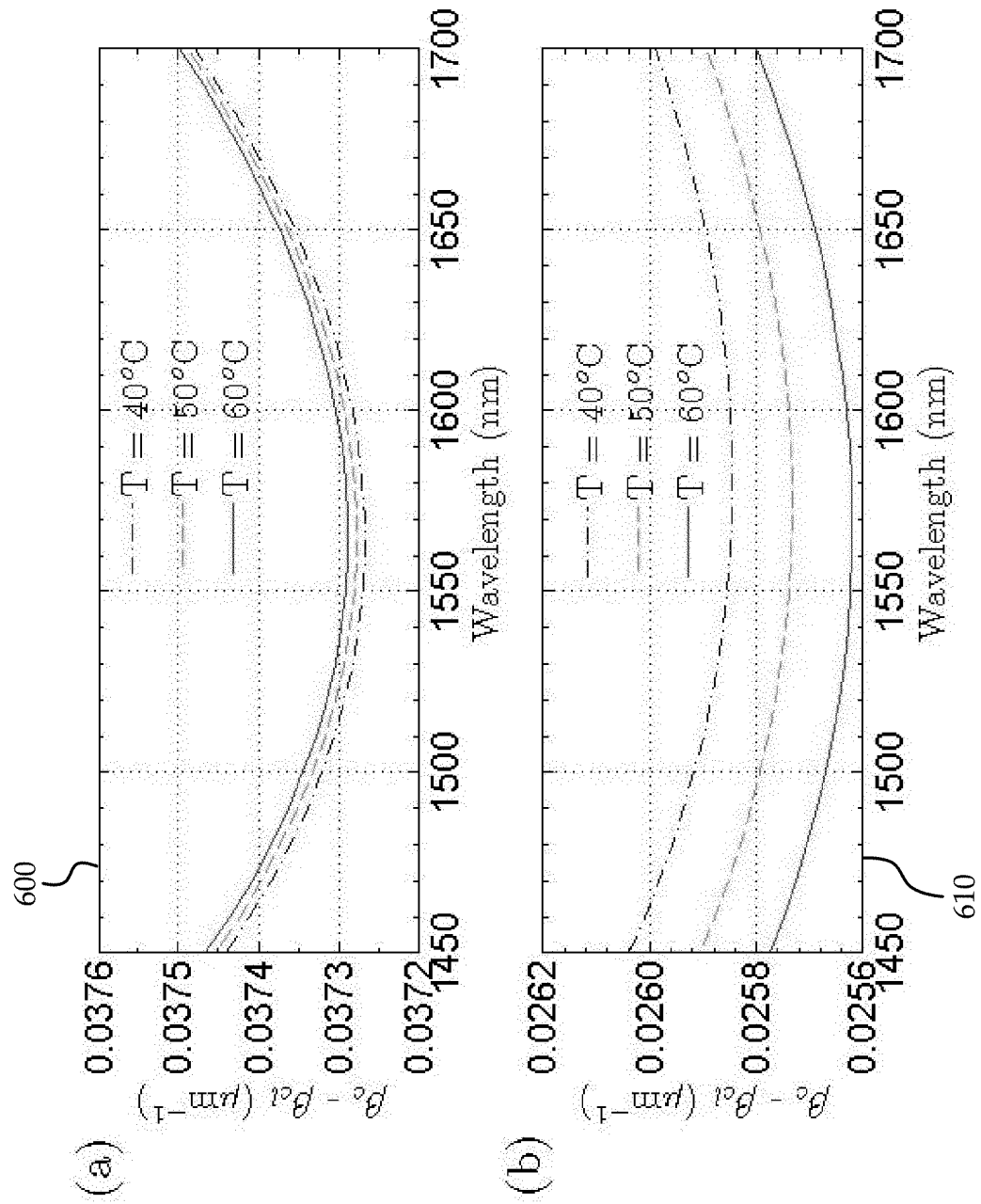
FIG. 6 shows (a) a graph illustrating measurements of the spectral variation of the propagation constant difference between the core mode and the cladding mode of a germaniosilicate fiber with a core composed of 4.1 mole % $GeO_2$ doped $SiO_2$; and (b) a graph illustrating measurements of the spectral variation of the propagation constant difference between the core mode and the cladding mode of a germaniosilicate fiber with a core composed of 9.7 mole % $B_2O_3$ in 4.03 mole % GeO2.

Another distinct feature illustrated in FIG. 6 is that the temperature-induced variation in $\Delta \beta$ is much larger for fiber-B than for fiber-G. This means that a relatively small length l of fiber-B can compensate the thermal shifts introduced by the gratings in fiber-G.

Figure 7:
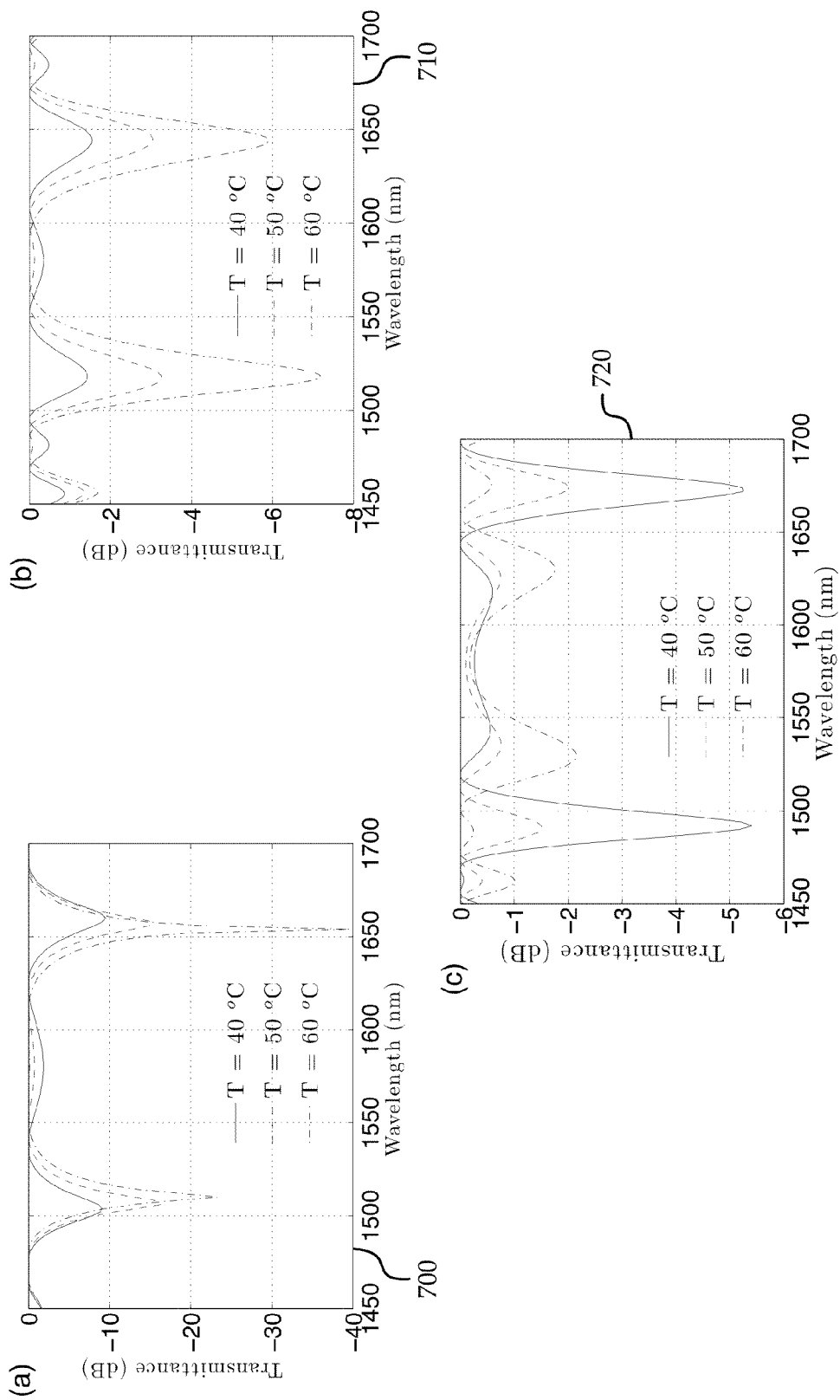
FIG. 7 shows (a) a graph illustrating calculations of the transmission spectrum of a sensor consisting of two DRLPGs in fiber-G separated by 4 mm of fiber-B; (b) separated by 6.5 mm of fiber-B; and (c) separated by 9 mm of fiber-B.

To generally investigate mathematically the transmission spectra of embodiments such as that depicted in FIG. 5, standard matrix method based on coupled mode theory where the field amplitudes of the core ($A_c$) and cladding modes ($A_{cl}$) at the input and output of the sensor are connected by Eq. [2] was used. FIG. 7 shows the simulated transmission spectrum of the sensors consisting of two DRLPGs 540, 560 separated by various lengths l of IGS 550 composed of fiber-B. The grating period, grating strength and grating length have been taken as 166.83 µm, 0.44×10⁻⁴ and 4 cm, respectively. Complete temperature insensitivity on either side of $\lambda_D$ is evident in graph 710 of FIG. 7(b) for l=6.5 mm, whereas for l=4 mm depicted in graph 700 of FIG. 7(a), the transmission spectrum shows a red spectral shifts for $\lambda<\lambda_D$ and blue shift for $\lambda>\lambda_D$ with increasing temperature. On the other hand, for l=9 mm depicted in graph 720 of FIG. 7(c), the transmission spectrum shows just opposite trend as compared to the sensor consisting of l=4 cm: blue spectral shifts for $\lambda<\lambda_D$ and red shift for $\lambda>\lambda_D$ with increasing temperature. The typical transmission behavior of the DRLPGs, namely a larger spectral shift for the transmission peaks/dips closest to the $\lambda_D$ is also evident from these figures.

With the predicted appropriate length of inter-grating fiber spacing IGS 550 an experimental study was conducted to verify predictions and refine the optical sensor. Such experiments are discussed with reference to FIG. 8.

Several DRLPGs 540, 560 were fabricated in widely used germaniosilicate single mode fiber Corning SMF-28™. For the ease of grating fabrication, the fibers were loaded with molecular hydrogen at 150 bar for 15 days. Photosensitive gratings were then inscribed to the core region of the fiber using a chromium amplitude mask ($\Lambda$=226.8 µm) and KrF excimer laser (Lumonics Lasers: Pulse Master-840™) emitting at 248 nm at a pulse repetition rate of 100 Hz, pulse duration of 12 ns, and peak pulse energy of 300 mJ. The gratings were then annealed at 150° C. for ~4 h to release the excess hydrogen, stabilizing their optical properties. The grating period and length of the LPGs so fabricated are 226.8 µm and 4 cm, respectively. After thermal annealing, the transmission spectrum of the LPGs was tuned to the dual-resonance regime by the partial cladding etching method. The RI and temperature sensitivities of the individual DRLPGs were then measured. The typical RI and temperature sensitivities of the LPGs used in the experiments are 1837 nm/RIU (2464 nm/RIU) and 0.95 nm/° C. (1.03 nm/° C.), respectively, for the $\lambda_R$~1557 nm (1627 nm).

Figure 8:
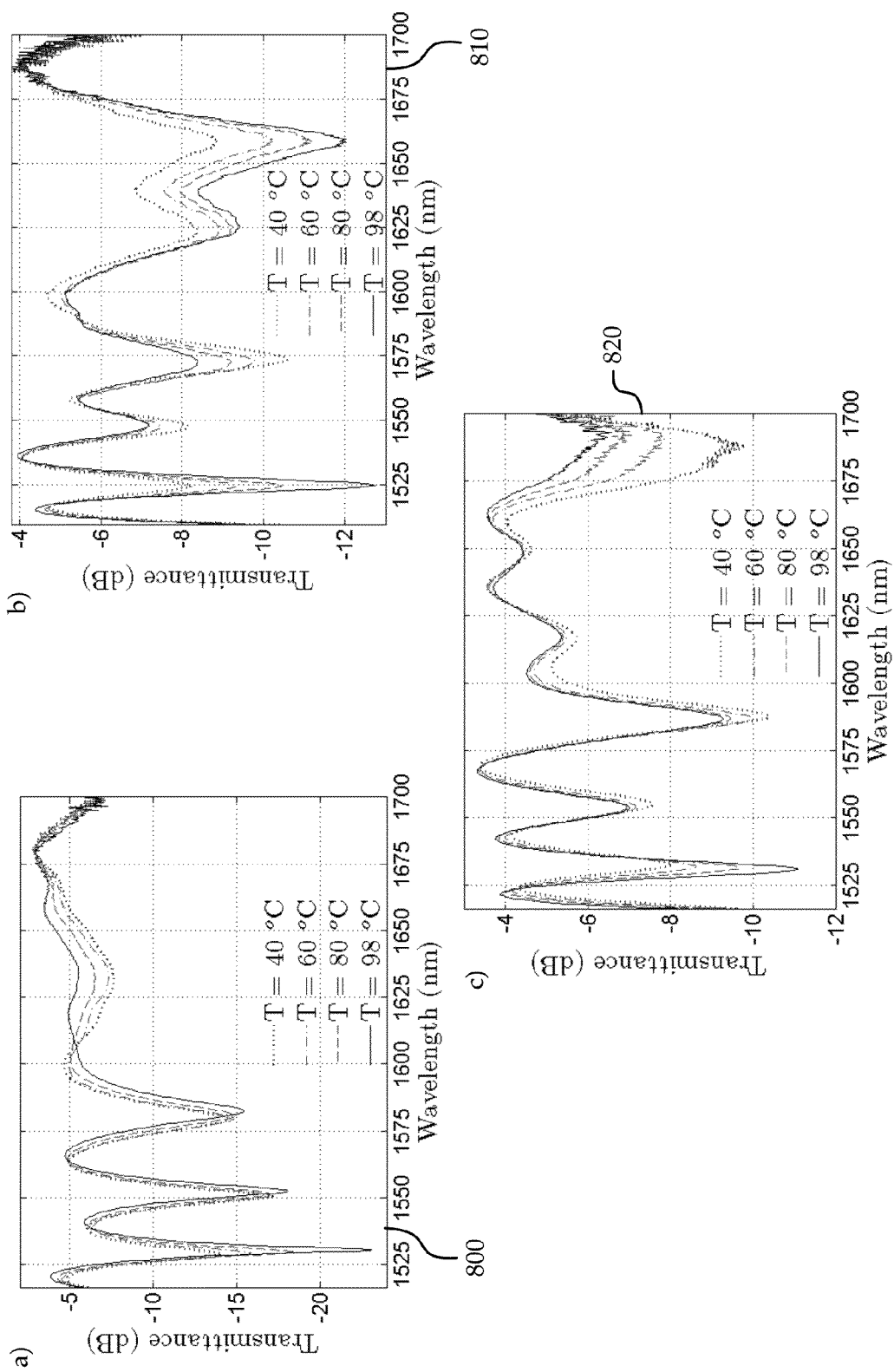
FIG. 8 shows graphs illustrating the experimental transmission spectrum of an optical sensor as shown in FIG. 5, specifically consisting of two DRLPGs in fiber SMF-28™ with an inter-grating fiber spacing of Boron doped PS-1200/1550 of a) 7.5 mm; b) 8.9 mm; and c) 10 mm.

Two DRLPGS with identical transmission spectra were selected and spliced axially with varying length (l) of $B_2O_3$ doped germanosilicate fiber Fibercore PS-1250/1500™ in-between them. The sensor was finally passed through a heating tube filled with water to measure its temperature response. In FIG. 8 there is plotted the transmission spectrum of the sensor for three different l values. As can be observed from graph 800 of FIG. 8(a) and graph 820 of FIG. 8(c), in agreement with the mathematical predictions, for smaller l (=7.5 mm) the transmission spectrum shows a red spectral shifts for $\lambda<\lambda_D$ and blue shift for $\lambda>\lambda_D$ and for relatively larger l (=10 mm) the transmission spectrum shows a blue spectral shifts for $\lambda<\lambda_D$ and red shift for $\lambda>\lambda_D$. The complete temperature insensitivity is obtained for l=8.9 mm over the entire wavelength range, as shown in graph 810 of FIG. 8(b), which is a wide wavelength range on the order of $10^2$ nm and higher.

It should be mentioned here that the slight disagreement between the mathematical value of the length of the IGS (l=6.5 mm) and the experimental one (l=8.9 mm) can be attributed to the slight difference between the mathematical and experimental fiber and grating parameters.

Figure 9:
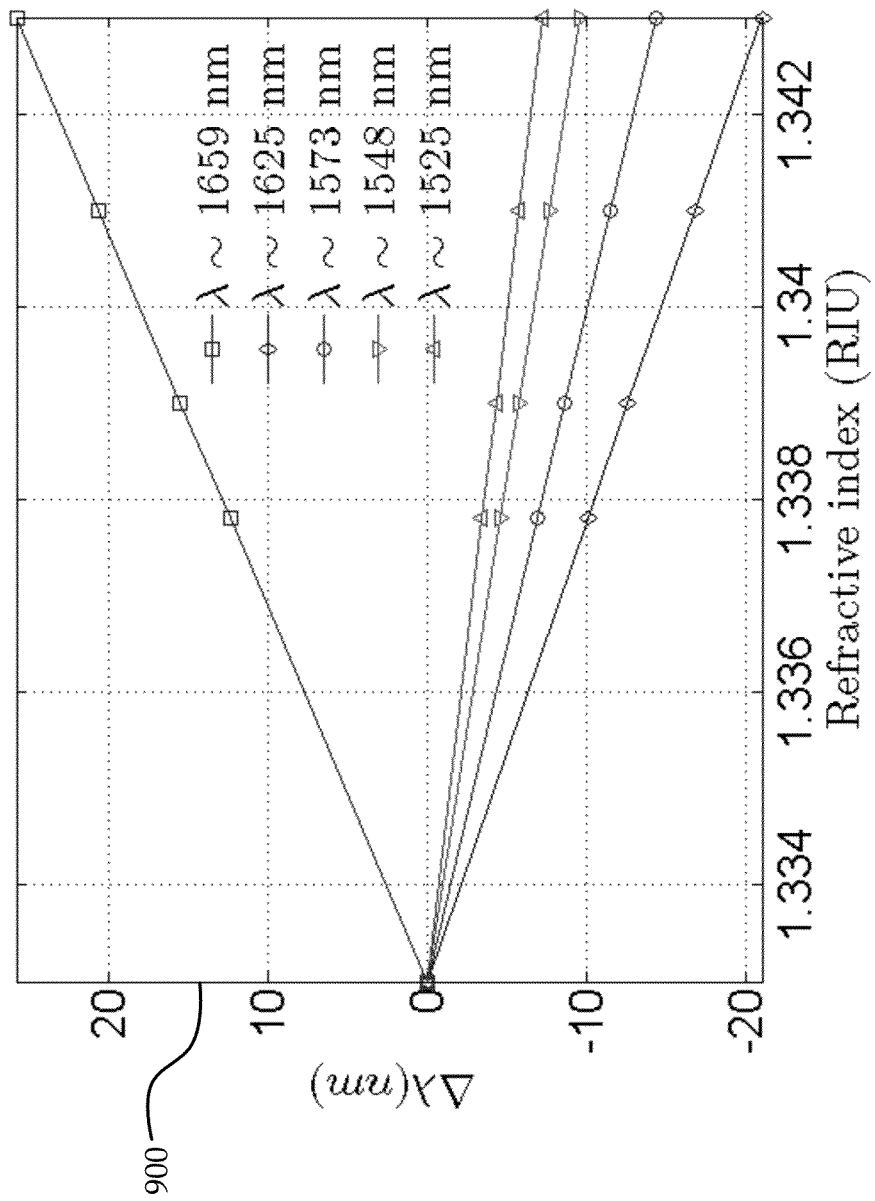
FIG. 9 shows graphs illustrating the experimental RI sensitivities corresponding to the resonance minima at 1525 nm, 1548 nm, 1573 nm, 1625 nm, and 1659 nm, for the temperature insensitive sensor having an IGS of 8.9 mm.

Finally, for the temperature insensitive sensor the spectral shifts of various transmission minima as a function of the ambient refractive indices (ARI) over the biologically relevant RI range of 1.333 to 1.343 were measured. This has been plotted in graph 900 of FIG. 9, showing a maximum sensitivity of ~2577 nm/RIU obtained for the resonance minima near 1659 nm. In agreement with the spectral shifts observed for the individual DRLPGs, for other transmission minima ($\lambda<\lambda_D$) a negative spectral shift with increasing ambient RI was observed. The sensitivities of the successive minima being −2104 nm/RIU, −1436 nm/RIU, −970 nm/RIU and −716 nm/RIU, respectively. Utilizing the enhanced sensitivity of the DRLPG by defining the overall sensitivity as the spectral change in the wavelength difference between the two closest minima on either side of $\lambda_D$, $$Sens. = \frac{\Delta(\lambda_2 - \lambda_1)}{\Delta n_{sc}} = \frac{|\Delta\lambda_2| + |\Delta\lambda_1|}{\Delta n_{sc}},$$

the RI sensitivity of the sensor becomes 4681 nm/RIU, which is the highest reported refractive-index sensitivity of the sensors based on LPGs. Assuming an optical detector with a resolution of 1 pm, the sensor is capable of measuring changes as small as 2×10⁻⁷ RIU in the bio-analyte over an ambient RI range of 1.333 to 1.343.

In order to analytically consider net zero temperature sensitivity, first consider a structure consisting of only optical fiber component portion. If $\Delta\beta_1$ is the propagation constant difference between first two dominant modes (core and cladding) then the phase difference ($\phi_1 = L_1\Delta\beta_1$) accumulated between them, at the end of the component portion, is a function of both the operating wavelength ($\lambda$) as well as the temperature (T). The change in $\phi_1$ due to a change in T and $\lambda$ is given by, $$\Delta\Phi_1(T, \lambda) = \frac{\partial\Phi_1}{\partial T}\Delta T + \frac{\partial\Phi_1}{\partial\lambda}\Delta\lambda \qquad [5]$$

The shift in $\lambda$ corresponding to a peak or dip, due to a change in T, can be determined from $\Delta\phi_1 = 0$, giving the temperature sensitivity $\eta_1$ for the structure consisting of the single component portion as, $$\eta_1 = \frac{\Delta\lambda}{\Delta T} = -\frac{\partial\Phi_1}{\partial T}\left(\frac{\partial\Phi_1}{\partial\lambda}\right)^{-1} = -\frac{\alpha_1\Delta\beta_1 + \partial(\Delta\beta_1)/\partial T}{\partial(\Delta\beta_1)/\partial\lambda} \qquad [6]$$

where, $\alpha_1$ is the thermal expansion coefficient of the single component portion. Similarly the temperature sensitivity ($\eta_2$) of the a structure consisting of a second optical component portion only, will be given by:

$$\eta_2 = -\frac{\alpha_2\Delta\beta_2 + \partial(\Delta\beta_2)/\partial T}{\partial(\Delta\beta_2)/\partial\lambda} \qquad [7]$$

Now, connecting two types of optical component portions of lengths $L_1$ and $L_2$ in series, the total phase difference developed between the two modes is given by $\phi(T,\lambda) = L_1\Delta\beta_1 + L_2\Delta\beta_2$ and the corresponding temperature sensitivity $\eta$ will be:

$$\eta = -\left\{\frac{\partial(L_1\Delta\beta_1)}{\partial T} + \frac{\partial(L_2\Delta\beta_2)}{\partial T}\right\} \Big/ \left\{\frac{L_1\partial(\Delta\beta_1)}{\partial\lambda} + \frac{L_2\partial(\Delta\beta_2)}{\partial\lambda}\right\} \qquad [8]$$

Thus the condition for achieving the zero temperature sensitivity is given by:

$$\frac{\partial(L_1\Delta\beta_1)}{\partial T} = \qquad [9]$$

$$-\frac{\partial(L_2\Delta\beta_2)}{\partial T} \Rightarrow L_1\left(\alpha_1\Delta\beta_1 + \frac{\partial(\Delta\beta_1)}{\partial T}\right) = -L_2\left(\alpha_2\Delta\beta_2 + \frac{\partial(\Delta\beta_2)}{\partial T}\right)$$

Using Eq. [6] and [7] in Eq. [9], the required length ratio to achieve zero temperature sensitivity is given by, $$\frac{L_1}{L_2} = -\frac{\eta_2}{\eta_1}\left(\frac{\partial(\Delta\beta_2)}{\partial\lambda} \bigg/ \frac{\partial(\Delta\beta_1)}{\partial\lambda}\right) \qquad [10]$$

This can be used only as a rough approximation for analyzing the optical signals traversing the first DRLPG 540 and the IGS 550 and for some distance into the second DRLPG 560 as the optical signals are undergoing coupling while traversing the first DRLPG and recoupling while traversing the second DRLPG. As such the length attributed collectively to the DRLPGs 540, 560 needs to be considered an "effective" length, and hence the ratio of lengths only an "effective ratio". That being the case, the functional relationships between the propagation constant difference curves ($\Delta\beta$ v. $\lambda$) to achieve temperature insensitivity remains instructive.

As mentioned hereinabove the turn-around points ($\lambda_D$) for the propagation constant difference curves should coincide. This is clear from Eq. [10] as it is required for the ratio of lengths to remain positive definite. Furthermore, to minimize the divergence in temperature insensitivity, the denominator in Eq. [8] should remain much greater than the numerator in Eq. [8] for as much of the wavelength spectrum as possible.

From Eq. [9] and taking into account that the typical thermal expansion coefficients are order(s) of magnitude smaller than the typical partial derivative of the propagation constant difference with temperature, the choice of lengths are largely determined by the partial derivative of the propagation constant difference with temperature, and as described hereinabove, a relatively large temperature dependence for the IGS 550 (as shown in FIG. 6(b)) compared to that of the DRLPG 540 (as shown in FIG. 6(a)) results in a much smaller length IGS 550 being required to compensate for temperature sensitivity of the DRLPGs 540, 560 than otherwise would be required.

Finally, from Eq. [10] the ratio of the slopes of the propagation constant difference curves (versus wavelength) should remain relatively constant over a wide wavelength range for substantial temperature insensitivity to obtain over that wide wavelength range.

Although the embodiments have been described in respect of a particular portion of the optical sensor 500 being doped with Boron, namely the core of the IGS 550, it should be understood that other kinds of doping which bring about the same kinds of relative dn/dT as discussed above are possible. Moreover, although the IGS 550 has been described as having a lower dn/dT in the core than in the cladding, and the DRLPGs have been described as having a higher dn/dT in their cores than in their cladding, the reverse is also possible. For example, a sensor may be comprised of DRLPGs which have Boron doped cores and an IGS with no Boron doping, as long as they have been dimensioned appropriately for the functional requirements to cause substantial temperature insensitivity, e.g. coincidental turn-around point, constant ratio of slopes, opposite sign of temperature dependence.

The above describes and demonstrates a wide-wavelength range temperature insensitive, extremely sensitive refractive-index optical sensor for bio/chemical sensing applications. The temperature insensitivity is obtained over the entire spectrum of DRLPG, on both sides of turn-around wavelength of the DRLPGs, in one embodiment by choosing a $B_2O_3$ doped germanosilicate fiber as the IGS material and adjusting its length to compensate for the spectral shifts arising within the DRLPG regions. With the highest ever reported sensitivity for the LPG based sensors (~4681 nm/RIU) the above described example sensor is capable of measuring changes as small as $2\times10^{-7}$ RIU in the bio-analyte over the biologically relevant ambient RI range of 1.333 to 1.343. The optical sensor shows a considerable reduction in the overall sensor length and the wide-range of temperature insensitivity (over 1500-1700 nm), which is also suitable for various other applications like temperature-insensitive WDM channel isolation filter etc.

While the present invention has been described in detail by way of the embodiments thereof, it should be understood that these embodiments are merely illustrative of the technical principles of the present invention but not limitative of the invention. The scope of the present invention is limited only by the appended claims.

The invention claimed is:

1. A fiber based optical sensor for measuring refractive index (RI), the optical sensor comprising:
   a plurality of dual resonant long period grating fiber portions (DRLPG), each having DRLPG core and DRLPG cladding; and
   an inter-grating fiber spacing (IGS) optically coupled between the plurality DRLPGs, having an IGS core and an IGS cladding such that a difference between an overall thermo-optic coefficient (dn/dT) of the IGS core and a dn/dT of the IGS cladding, is of a sign opposite to a difference between a dn/dT of the DRLPG core and a dn/dT of the DRLPG cladding, the length of the IGS being such that the optical sensor exhibits an overall temperature insensitivity over a wide wavelength range.

2. An optical sensor according to claim 1 wherein the IGS comprises $B_2O_3$ doped germaniosilicate core fiber.

3. An optical sensor according to claim 2 wherein each DRLPG is fabricated from germaniosilicate core fiber.

4. An optical sensor according to claim 3 wherein the IGS cladding and the DRLPG cladding each comprise $SiO_2$, and wherein the DRLPG core comprises $GeO_2$, such that the difference between the (dn/dT) of the IGS core and the dn/dT of the IGS cladding is negative, and the difference between the dn/dT of the DRLPG core and the dn/dT of the DRLPG cladding is positive.

5. An optical sensor according to claim 3 wherein a temperature dependence of the propagation constant difference curve of the IGS doped with $B_2O_3$ is larger than a temperature dependence of the propagation constant difference curve of the plurality of DRLPGs.

6. An optical sensor according to claim 1 wherein the IGS core comprises $GeO_2$, each DRLPG core comprises $B_2O_3$, and the IGS cladding and the DRLPG cladding each comprise $SiO_2$, such that the difference between the (dn/dT) of the IGS core and the dn/dT of the IGS cladding is positive, and the difference between the dn/dT of the DRLPG core and the dn/dT of the DRLPG cladding is negative.

7. An optical sensor according to claim 6 wherein turn-around points of the propagation constant difference curves of the IGS and the plurality of DRLPGs are substantially equal.

8. An optical sensor according to claim 6 wherein the plurality of DRLPGs comprise two DRLPGs.

9. An optical sensor according to claim 6 wherein the plurality of DRLPGs comprise two DRLPGs and wherein turn-around points of the propagation constant difference curves of the IGS and the plurality of DRLPGs are substantially equal.

10. An optical sensor according to claim 6 wherein a ratio of a slope of a propagation constant difference curve of the IGS to a slope of a propagation constant difference curve of the plurality of DRLPGs is substantially constant over the wide wavelength range.

11. An optical sensor according to claim 6 wherein a ratio of a slope of a propagation constant difference curve of the IGS to a slope of a propagation constant difference curve of the plurality of DRLPGs is substantially constant over the wide wavelength range, and wherein turn-around points of the propagation constant difference curves of the IGS and the plurality of DRLPGs are substantially equal.

12. An optical sensor according to claim 6 wherein a ratio of a slope of a propagation constant difference curve of the IGS to a slope of a propagation constant difference curve of the plurality of DRLPGs is substantially constant over the wide wavelength range, wherein the plurality of DRLPGs comprise two DRLPGs, and wherein turn-around points of the propagation constant difference curves of the IGS and the plurality of DRLPGs are substantially equal.

13. An optical sensor according to claim 12 wherein the IGS comprises single mode PS-1250/1500™ fiber, each DRLPG comprises standard SMF-28™ fiber, a period of the gratings of the DRLPGs is 226.8 µm, each DRLPG is 4 cm in length, and the IGS is 8.9 cm in length.

14. An optical sensor according to claim 13 wherein the core radius of the IGS is substantially equal to 4.95 µm, the cladding radius of the IGS is substantially equal to 62.5 µm, the core radius of the DRLPGs is substantially equal to 4.1 µm, the unetched cladding radius of the DRLPGs is substantially equal to 62.5 µm, and the etched cladding radius of the DRLPGs is substantially equal to 55 µm.

15. An optical sensor according to claim 1 wherein turn-around points of the propagation constant difference curves of the IGS and the plurality of DRLPGs coincide.

16. An optical sensor according to claim 15 wherein the wide wavelength range is substantially 100 nm on either side of the turn-around points of the propagation constant difference curves of the IGS and the plurality of DRLPGs.

17. An optical sensor according to claim 15 wherein a ratio of a slope of a propagation constant difference curve of the IGS to a slope of a propagation constant difference curve of the plurality of DRLPGs is substantially constant over the wide wavelength range.

18. An optical sensor according to claim 1 wherein turn-around points of the propagation constant difference curves of the IGS and the plurality of DRLPGs are substantially equal.

19. An optical sensor according to claim 18 wherein the plurality of DRLPGs comprise two DRLPGs.

20. An optical sensor according to claim 18 wherein a ratio of a slope of a propagation constant difference curve of the IGS to a slope of a propagation constant difference curve of the plurality of DRLPGs is substantially constant over the wide wavelength range.

21. An optical sensor according to claim 1 wherein the wide wavelength range is 200 nm.

22. An optical sensor according to claim 1 wherein the plurality of DRLPGs comprise two DRLPGs.

23. An optical sensor according to claim 22 wherein a ratio of a slope of a propagation constant difference curve of the IGS to a slope of a propagation constant difference curve of the plurality of DRLPGs is substantially constant over the wide wavelength range.

* * * * *